United States Patent [19]
Garcia

[11] Patent Number: 6,088,429
[45] Date of Patent: *Jul. 11, 2000

[54] INTERACTIVE TELEPHONY SYSTEM

[75] Inventor: Alfredo Garcia, deceased, late of Philadelphia, Pa., by Badra Berkane, legal representative

[73] Assignee: Mumps Audiofax, Inc., Wayne, Pa.

[*] Notice: This patent is subject to a terminal disclaimer.

[21] Appl. No.: 09/056,582

[22] Filed: Apr. 7, 1998

[51] Int. Cl.[7] ........................................... H04M 1/64

[52] U.S. Cl. .................. 379/88.22; 379/67.1; 379/93.12

[58] Field of Search ............................... 379/67.1, 74, 77, 379/88.11, 88.16, 88.17, 88.18, 88.22, 88.23, 88.24, 88.25, 90.01, 93.12, 93.13, 101.01, 201; 364/400

[56] References Cited

U.S. PATENT DOCUMENTS

| | | | |
|---|---|---|---|
| 4,539,435 | 9/1985 | Eckmann | 179/2 A |
| 4,766,542 | 8/1988 | Pilarczyk | 364/413 |
| 4,847,764 | 7/1989 | Halvorson | 364/413 |
| 4,899,839 | 2/1990 | Dessertine | 177/25.19 |
| 5,016,172 | 5/1991 | Dessertine | 364/413.02 |
| 5,164,981 | 11/1992 | Mitchell et al. | 379/88 |
| 5,199,062 | 3/1993 | Von Meister et al. | 379/67 |
| 5,225,976 | 7/1993 | Tawil | 364/401 |
| 5,299,121 | 3/1994 | Brill et al. | 364/413 |
| 5,329,459 | 7/1994 | Kaufman et al. | 364/479 |
| 5,337,347 | 8/1994 | Halstead-Nusslock et al. | 379/67 |
| 5,345,501 | 9/1994 | Shelton | 379/89 |
| 5,390,238 | 2/1995 | Kirk et al. | 379/93 |
| 5,404,295 | 4/1995 | Katz et al. | 364/419 |
| 5,454,063 | 9/1995 | Rossides | 395/2.84 |
| 5,509,064 | 4/1996 | Welner et al. | 379/265 |
| 5,544,229 | 8/1996 | Creswell et al. | 379/67.1 |
| 5,594,638 | 1/1997 | Ilif | 395/203 |
| 5,612,869 | 3/1997 | Letzt et al. | 395/203 |
| 5,737,396 | 4/1998 | Garcia | 268/88 |
| 5,825,856 | 10/1998 | Porter et al. | 379/88 |

OTHER PUBLICATIONS

"Method of Automating the Dictation and Transcription Functions of a Radiology Department", IBM TDB, Jun., 1991.

MUMPS AudioFAX Trade Literature entitled "DHCP–Rx/INFO", Jul. 6, 1994 (limited distribution).

Veterans' Administration invoice for "Order No. 402–A37635", Aug. 16, 1994.

"Walgreens continues to set the standard for drug chains, Pleans to increase its Market Share & Boost Customer Convenience", Chain Drug Review, p. 75, dated May 1, 1995.

"High–Tech Rx for Walgreen Pharmacies, Will roll out a high–tech Pharmacy system in Apr. 1995 that it expects to revolutionize the industry", Chicago Sun Time (IL), p. 49, dated Jan. 12, 1995.

"Walgreens, Arbor set new benchmarks: Industry's top chain notches 20th record year, Net Income Jumped 14.9% to 281.9 Mil. in FY 1994", Drug Store News, p. 15, James Frederick, dated Oct. 24, 1994.

*Primary Examiner*—Scott L. Weaver
*Attorney, Agent, or Firm*—Duane Morris & Heckscher LLP

[57] ABSTRACT

Interactive medication data systems and methods are provided which include automated means for providing information pursuant to telephonic and electronic requests from callers. The system includes a database containing information for patients and a variety of medications, a host system database containing prescription data for these medications, and means for receiving an incoming audio communication relating to a request for information concerning a specific medication. The audio communication contains a unique personal identifier which can be mapped to one patient in the host system database. The system then prompts the caller with a menu of selections relating to the patient's active prescriptions, such as, refill or dosage requirements. The caller then selects an option which produces a selection signal. The selection signal guides the system to look for specific data in the database and the system produces an audio or visual response to the caller.

22 Claims, 4 Drawing Sheets

INTERACTIVE TELEPHONY SYSTEM

This application pertains to the general field of U.S. Pat. No. 5,737,396.

FIELD OF THE INVENTION

This invention relates to telephony systems for conveying audio information among patients, health care providers, pharmacy personnel and others.

BACKGROUND OF THE INVENTION

Verbal information dispensed from physicians and pharmacists is often easy to forget, and patients often misplace, or find it difficult to understand written materials.

Efforts to automate the dispensing of medication information have included the use of 900 numbers for ordering printed drug information, or for conferencing with a live person for obtaining answers to specific inquiries. Medication information software has also been developed which can respond to the spelling of medication names with textual information.

Individual drug companies have additionally created telephony systems which receive requests for information for specific drugs. Such systems are generally limited to providing highly technical reports for practitioners about medications from a specific manufacturer.

While current efforts to automate the medication information process have had some limited success, there is a present need for a more comprehensive system for communicating important information relating to side effects, usage and general information for medications of every sort, independent of the specific manufacturer. There also remains a need for an interactive medication information system which provides immediate, on-demand answers to important questions of users at a level easily understood by the lay user and that is simple to use.

A BRIEF DESCRIPTION OF THE DRAWINGS

The accompanying drawings illustrate preferred embodiments of the invention according to the practical application of the principles thereof, and in which:

FIG. 1: is a diagrammatic flow diagram of an interactive medication information telephony system which is described in detail in my earlier application Ser. No. 08/786,088, which is incorporated by reference herein.

FIG. 2: is a flow chart diagram of an improved interactive medication information telephony system.

SUMMARY OF THE INVENTION

The present invention is an automated telephony method and system for providing information relating to a patient in response to an incoming audio communication from a caller. A database is provided, containing information representing attributes of each of a plurality of patients. An incoming audio communication is received via a telecommunications network. The audio communication contains a unique identifier which is associated with a specific one of the patients in the database. A list of selectable operations are identified to the caller. The list of selectable operations is specific to the specific patient. The caller selects one of the selectable operations, and a selection signal is provided. The system matches the selection signal with a portion of the medical information in the database relating to the specific patient. An output is provided to the caller. The output is representative of the portion of information relating to the specific patient.

GLOSSARY OF TERMS

"audio communication"—a signal representing an audible sound, which can be regenerated into a sound if needed.

"telephony"—relating to computer-controlled processing of audio communications over a telephone network.

"mapping" or "mapped"—a process whereby existing associations between identifiers and targets are used to always resolve to the same target for a given identifier.

"usage"—background information relating to a given medication which may include general topics, such as why the medication is prescribed, how to store and administer the medication, what to do if a scheduled dose is skipped, etc.

"host system"—when the IVR functions are considered peripheral to functions performed on a separate system unit, and the IVR system relies on the separate system unit for data necessary for the IVR functions, then the separate system is called a "host system."

"pharmacy management system"—an automation technology used to manage processes relevant to the dispensation of medications to patients based on prescriptions generated by health care providers.

"telephonic audio inquiry"—an audio communication received over a telephone network that maps to a specific inquiry intended by the originator of said audio communication, such that said inquiry can be processed, directly or indirectly, by the IVR system, with the intention of eventually responding to said inquiry by the IVR system in a manner intelligible to or specified by the originator.

OVERVIEW

The present invention is an improvement over a system described and claimed in U.S. patent application Ser. No. 08/786,088, which is incorporated by reference herein in its entirety.

Figure 1:
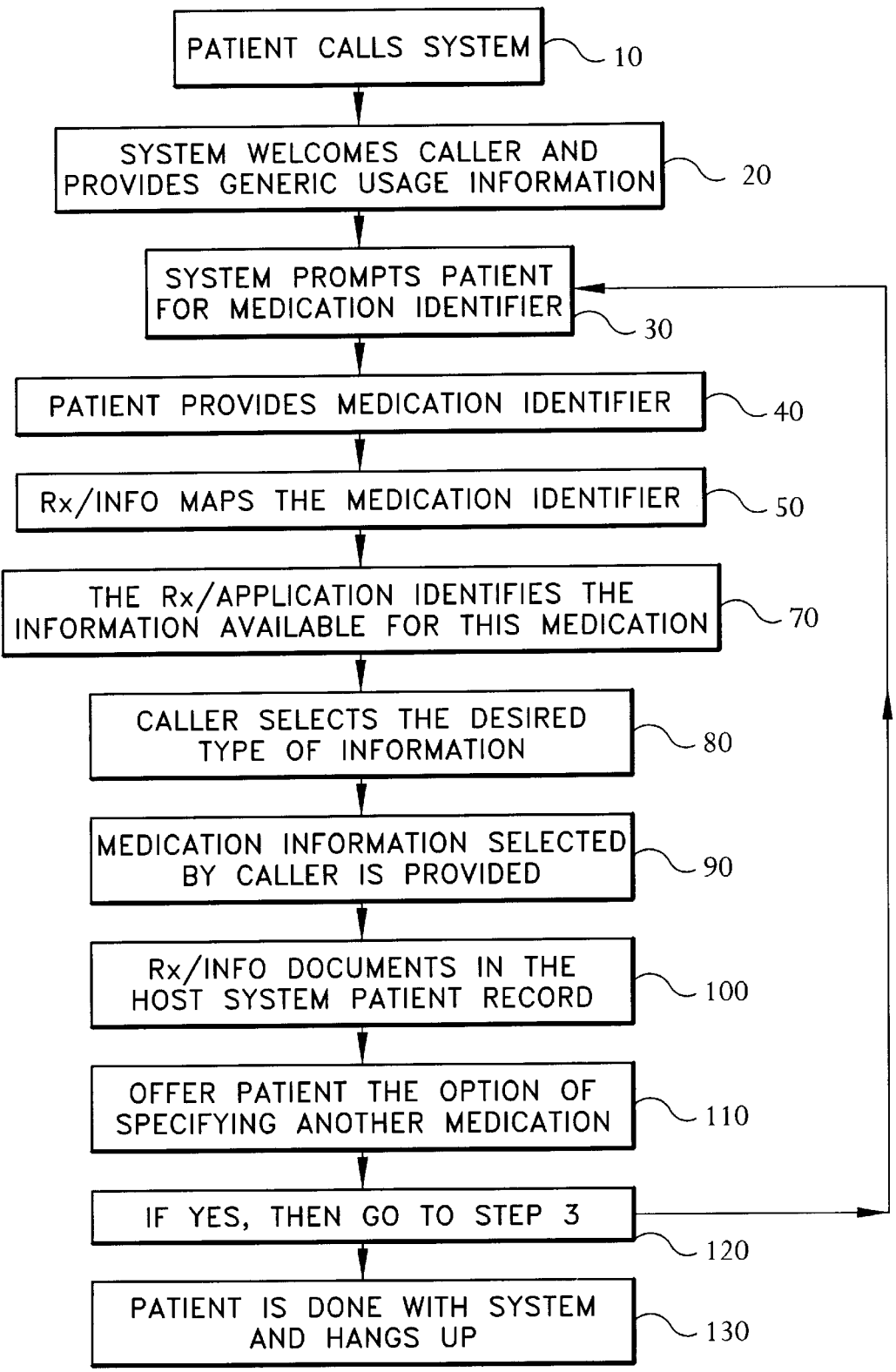
Figure 2:
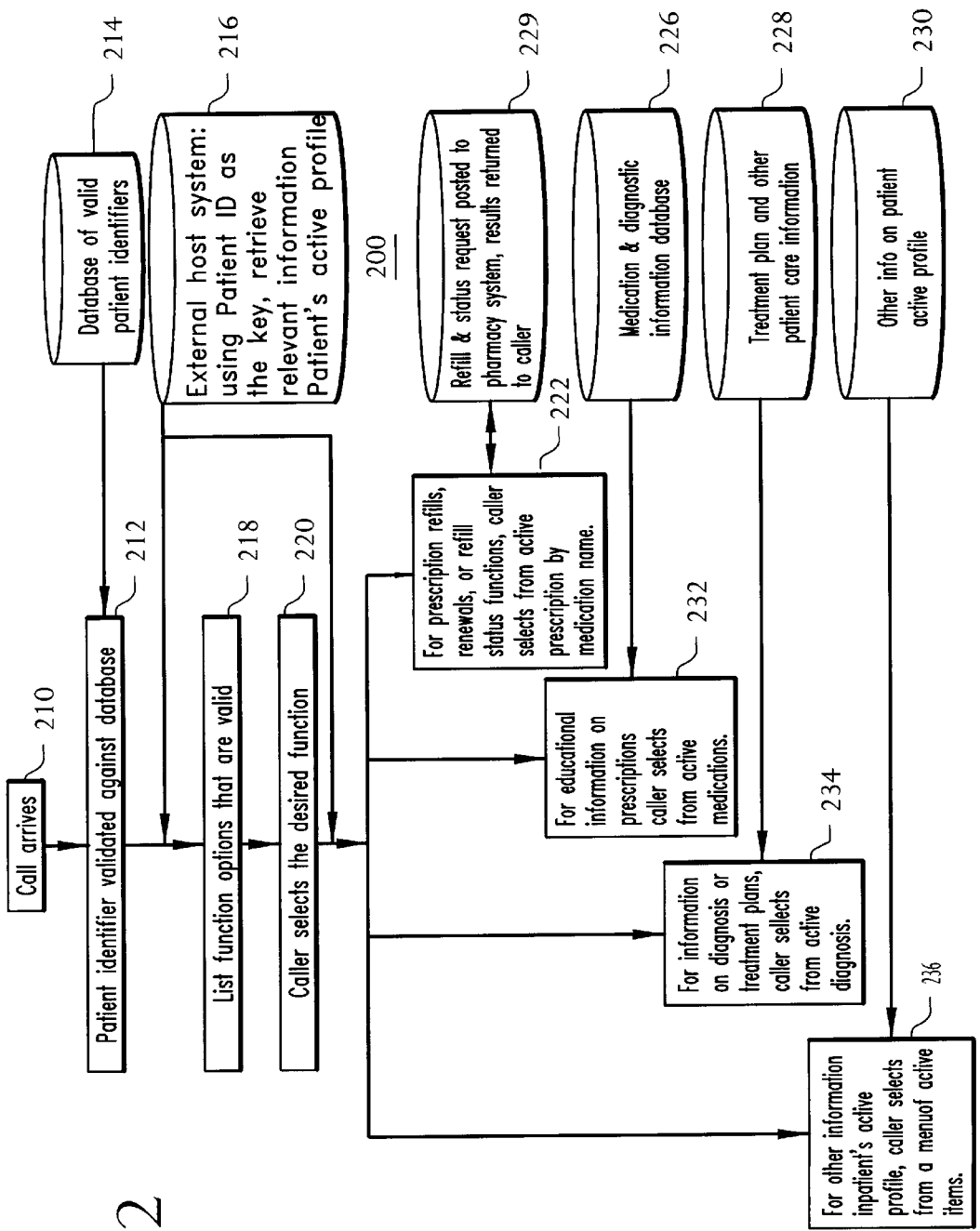
Figure 3:
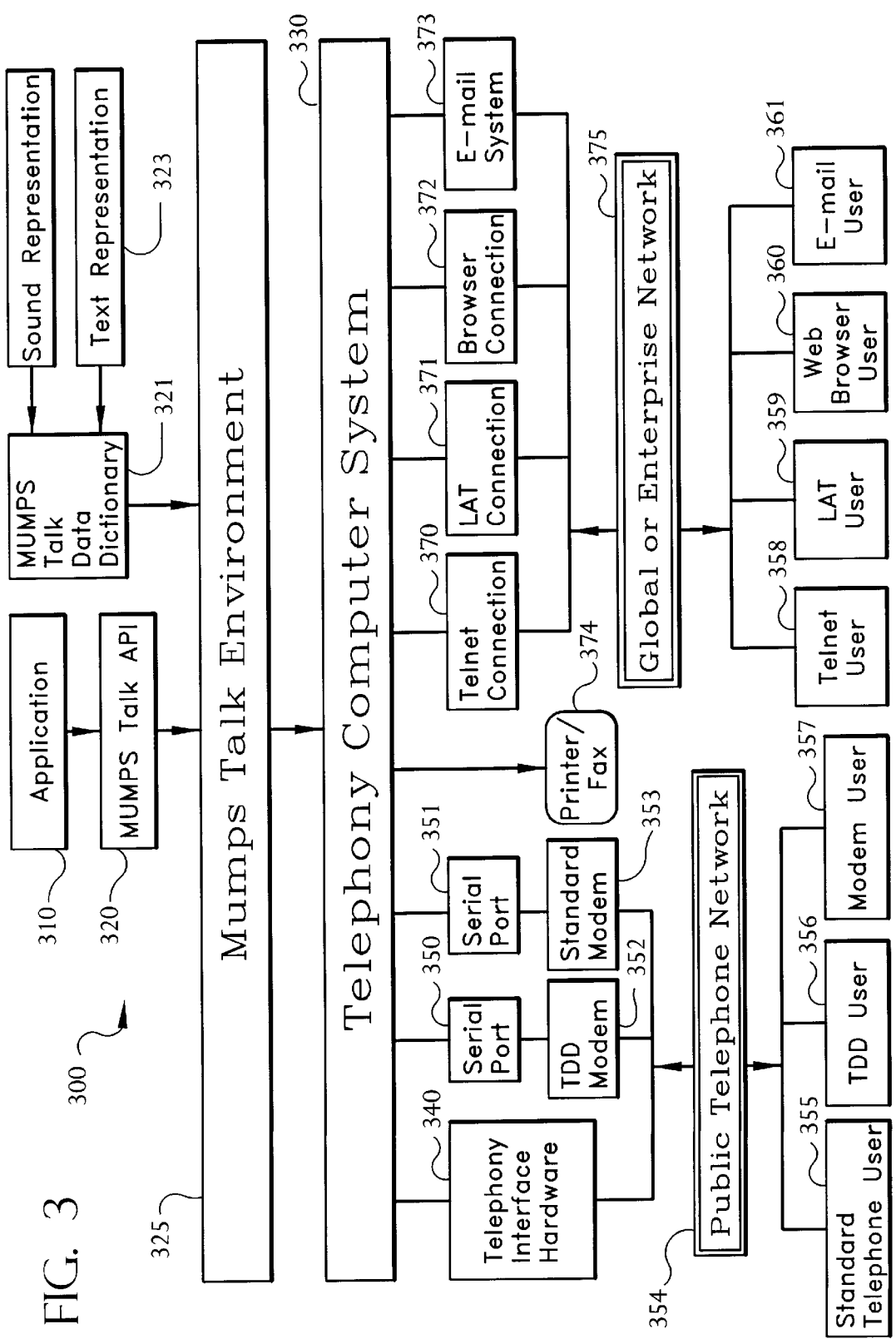
FIG. 3 is a block diagram of an exemplary system according to the present invention.

FIGS. 2 and 3 show an automated telephony method and system 300 for providing information relating to a patient in response to an incoming audio communication from a caller.

The caller may be the patient, or another individual acting on behalf of the patient, or an automated system designed to interface with a system 300 according to the present invention. Preferably, the caller uses a device for audio communication such as a standard telephone 355, or telephone device for the deaf (TDD) 356. Other calling means may also be used, such as a modem 357 for connecting to a computer or terminal (not shown), a remote computer or terminal 358 communicating via a Telnet connection, an LAT connection 359, or a web browser 360 which communicates via a global communications network, such as the Internet. In a preferred embodiment of the invention, a telephony server 330 is provided which is capable of receiving inputs from, and providing outputs to, any of the types of calling devices, including telephone 355, TDD 356, modem 357, Telnet terminal 358, LAT 359 or browser 360. Further, if the caller is using a telephone 355, the caller may either answer via speaking into the telephone, or by using a standard Dual Tone Multi-Frequency (DTMF) keypad.

One or more databases 214 are used by the exemplary system 300. At least one database 214 contains information representing attributes of each of a plurality of patients. Preferably, this database is organized to provide a "patient profile" which includes a variety of data relating to the patient's health, conditions, treatment plan, medical history and a list of medications taken by the patient. The medications may further be categorized as: active (currently being taken) or inactive (not currently being taken), and prescription or non-prescription. The database may be a distributed database. Alternatively, the desired information for the patient's profile may be stored in a plurality of different databases accessible by the system 300. For example, a patient's history of prescription medications may be stored in a distributed database including database 214 and external host database 216. Alternatively, the data may be concatenated from a plurality of databases, including a pharmacy database 224, a medication and diagnosis database 226, a treatment plan database 228 or other database 230, which may include lab test information, practice information, inpatient status and location or billing and appointment information.

FIG. 2 shows the details of an exemplary method.

At step 210, an incoming audio communication is received. The audio communication may come in a telephone call via a telecommunications network 354. The audio communication contains a unique patient identifier which is specifically associated with one of the patients in the database 214. This identifier may be used both to identify the patient to which the audio communication pertains and as a means of authentication to confirm that the caller is authorized to interact with the system 300. The system performs the authentication. The patient identifier may be based on an identifier that is globally unique to the patient (e.g., social security number). Alternatively, the identifier may be unique to a patient within the system 300. For example, if system 300 has a single pharmacy database, then a prescription number would be sufficient to uniquely identify a patient.

At step 218, the system 218 identifies a plurality of selectable operations from which the caller can select an operation via the telecommunications network. According to one aspect of the invention, the selectable operations identified are specific to the patient. Depending on who the patient is, the list of selectable operations may vary. There are potentially thousands of functions available, as is the case with diagnoses or medications. Different users may be authorized to access different operations. According to one aspect of the invention, a caller that is already familiar with possible operations for the specific identified patient may vocalize the selection of an authorized function, or the list of functions that are specific to the identified patient may be provided to the caller in the form of an audio signal transmitted to a standard telephone user 355.

At step 220, the caller selects one of the medical information categories listed in the menu, to provide a selection signal to system 300, causing control to transfer to either step 222, 232, 234 or 236 (corresponding to the respective information categories in databases 224, 226, 228 and 230). Once an operation is selected, the caller can select from a list of items. Once again, a caller that is already familiar with the system may vocalize the selection of an item, or the list may be provided to the caller in the form of an audio signal transmitted to a standard telephone user 355. The audio signal my include previously recorded speech, synthesized speech, or a combination of the two.

At step 222, 232, 234 or 236, the selection signal is matched against a portion of the medical information relating to the specific patient in the database 214. The system 300 provides an output to the caller which is representative of the requested portion of information. The output may be a message containing verbal drug information, such as information on medicine usage, side effects, precautions for a specific medication, health-related information concerning the patient's lifestyle, or general background information.

In the case of information concerning a medication, preferably the database contains information and unique signatures, or identifiers, for a variety of medications. For example, a component of the U.S. Pharmacopeial Convention's National Drug Code (NDC) may be used. The National Drug Code includes multiple components, a first component of which is generically used to identify a pharmaceutical, regardless of the manufacturer. Preferably, the National Drug Code's unique drug identification component would be printed in human-readable form on all medications. This would allow the caller to request data regarding the generic compound, or enter codes for multiple drugs to check on drug-to-drug interactions, with or without all of these medications being in the patient's profile. In addition, the caller may add medications to the patient's profile.

According to a further aspect of the invention, the system 300 determines whether the medication identified in the communication from the caller has an interaction with a further medication the patient is taking. This determination may be performed based on the plurality of data pertaining to the patient in the database, or additionally, based on medications identified by the caller while connected to the system. Thus, upon request by the caller for information regarding any medication not already listed as active in the patient's profile, system 300 checks for interactions between the medication for which information is requested and any active medication(s) in the patient's profile. If any interaction is identified, a warning is transmitted to the patient. The warning may specifically identify the two medications which may have an interaction and the possible results of the interaction, or the warning may advise the patient to consult with a pharmacist to review. Further it is possible to identify potential interactions between lab tests and medications in the patient's profile or otherwise identified by the patient.

Figure 4:
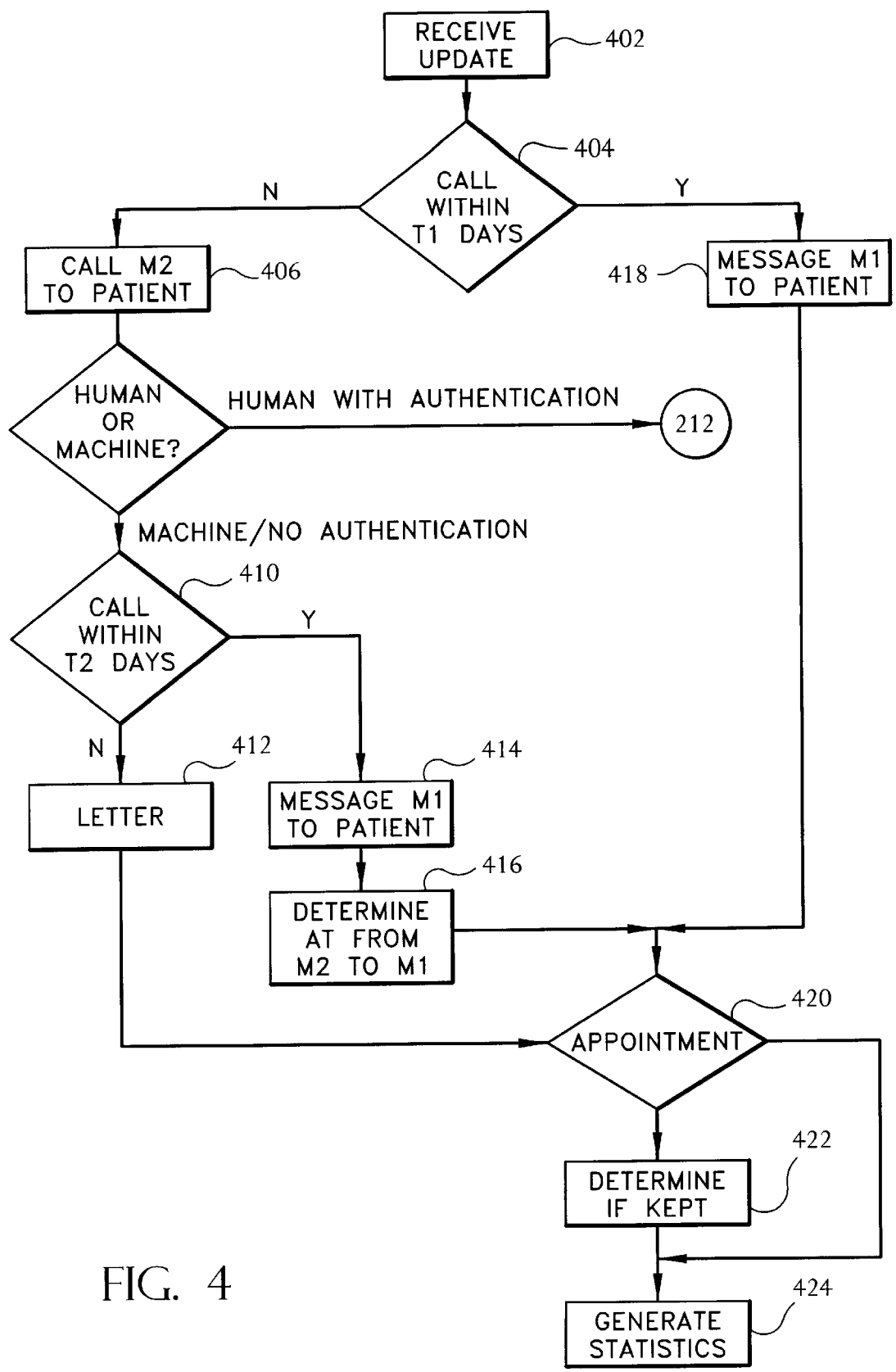
FIG. 4 is a flow chart diagram of an exemplary messaging function according to the invention.

FIG. 4 shows an additional capability of the system. According to a further aspect of the invention, the system 300 includes an advanced calling and reminder facility. The calling and reminder facility provides automated calling to patients, either to alert the patient to an update to the patient's profile (e.g., receipt of lab test results), or to remind the patient of an appointment the patient has scheduled.

Another aspect of this capability is the ability to post results back to the host application database. One example is the ability to record results of attempting to deliver messages to the patient, including: when a patient is not reached, a message is left, a patient has confirmed intention to attend, a patient indicates he/she will not attend, or a phone number is changed or incorrect. Posting back to the host system makes this information available to practice users from their principle application without having to access a separate source for this information. Further, this capability enables generation of reports that document the effectiveness of the application at reaching patients. Further, host users can see the results of their calls on the patient record on the host system.

At step 402, the system 300 receives an update to the patient profile and stores the update in the database 214. The update may, for example, be: the receipt of a test result, a message from the provider's staff, change in room location, a doctor's diagnosis, the need to refill a prescription, the approach of an impending appointment of the patient, disposition of a prescription renewal report, result of a referral request, or other event of interest to the patient.

At step 404, system 300 determines whether an audio communication (e.g., a telephone call) is received from the patient within a first predetermined period of time (T1 days, where T1 is an adjustable pre-set value stored in the database) after the update is received. (The audio communication is recognizable by the system as containing an identifier corresponding to the patient.). For example, the patient may call in on his own.

If the audio communication is received, then, at step 418, when the audio communication is received, the system automatically provides a first message M1, which includes information from the update. This message M1 is played back to the patient in the same format in which it is received. For example, if the patient calls in on a telephone, the message is vocalized back to the patient. If the patient uses a TDD, the message M1 is transmitted to the patient in TDD format.

If the communication is not received from the patient within T1 days after the status update is received, then at step 406, then a telephone call is automatically made to the patent, and a second message M2 is transmitted to the patient. The message M2 may, for example, notify the patient that an important message is available for the patient to review, and provide the patient with instructions for receiving the message. The message M1 is ordinarily not transmitted at this time, in order to maintain confidentiality. If, however, the party answering the call inputs an authentication to show that he/she is the patient, control is transferred to step 212 of FIG. 2, so that the message M1 can be delivered to the patient.

Optionally, the value of T1 may be pre-set to zero in the system, so that there is no waiting period between the receipt of the status update (by system 300) and the automatic call to the patient. In a variation of the exemplary embodiment, steps 404 and 418 may be omitted, and control would directly proceed from step 402 to step 406 in all cases. This would have the same effect as setting the value of T1 to zero.

Referring again to FIG. 4, at step 408, when the system 300 calls the patient to deliver message M2, the system 300 automatically determines whether the telephone call is answered by a human or a machine. This may be accomplished by, for example, measuring the length of the greeting when the patient's phone is answered, which is a well-known technique.

At step 410, the system collects data indicating whether and how soon the audio communication is received within a second predetermined period T2 after the message M2 is left for the patient in step 408.

At step 412, if the patient has not called in or otherwise responded within T2 days, system 300 automatically generates a letter or postcard that is sent to the patient. This letter has the address of the patient retrieved from the host database, and includes the actual text of the message M1.

At step 414, if the patient or caller does call in within T2 days, the message M1 is then delivered to the patient.

At step 416, the system calculates the time between leaving the message M2 for the patient in step 406 and receiving the audio communication from the patient in step 414.

At steps 420 and 422, if the status update is due to an approaching appointment of the patient (e.g., within one week), then the system makes a record of whether the appointment is kept by the patient.

At step 424, a plurality of statistics are calculated to demonstrate or measure the effectiveness of system interactions with the patients. For example, the statistics may be used to automatically determine whether the appointment is more likely to be kept when the telephone call is answered by a human at step 406 than when the telephone call is answered by a machine. The system may also automatically calculate statistics for an amount of time between the telephone call and the audio communication. This statistical analysis measures the effectiveness of the application based on how many patients are ultimately reached by the system. This enables users to discriminate the effectiveness of the system in reducing no-show rates for patients actually reached versus those that were called but not reached.

In addition to the capabilities set forth above, additional capabilities may be provided by system 300. For example, when calling in to the system, after receiving the message M1, the patient may receive a menu and provide a menu selection to the system indicating a preferred appointment time for the patient. The system can then automatically schedule an appointment for the patient on the host system based on the menu selection, and store the appointment in the database. The patient may request and receive information (as shown in FIG. 2). The patient may request a refill of a prescription using either prescription number, a patient ID plus a selection, or the National Drug Code.

These and other aspects of the invention are described in detail below, with reference to the exemplary embodiments and the attached Figures.

DETAILED DESCRIPTION OF THE INVENTION

As the inventor of the present application and another co-pending U.S. patent application, I hereby declare that any reference herein to my earlier filed application(s) and inventions, or comparison therewith, is made solely for the purpose of distinguishing the present invention from my earlier application, and to make clear that the present invention is patentably distinguishable from the disclosure of my earlier filed application. No reference herein to any of my earlier filed applications should be interpreted as an admission that my earlier filed applications are "prior art" as to the invention claimed herein.

TELEPHONY SYSTEM

Interactive automated telephony methods and systems are provided by this invention. The disclosed systems provide information relating to a patient (for example, any one of a plurality of medications prescribed for the patient) in response to an incoming audio communication from a caller. An identification of the patient is used as the database key for querying the database 214 to retrieve information concerning a variety of categories of medical information pertinent to the patient so identified.

The present invention provides easier use and higher accuracy than many prescription refill and refill status systems currently on the market. The present invention provides the first automated and interactive telephony system known to the inventor, in which refills, renewals, refill status and other pharmacy functions can be requested, without a prescription number, and in which these pharmacy functions are processed automatically by the host pharmacy system 300. By using a patient identifier, such as a voice print, security code, or social security number, for example, to identify the patient, the system 300 can provide a patient-specific list of active items from which the patient can make a selection. Furthermore, this invention greatly enhances the usability of known voice recognition techniques and enables use of voice recognition techniques to process pharmacy.

One embodiment (shown in FIG. 2) includes a database providing information for a variety of medications 214 and a host system database 216 containing information relevant to patients, including prescription data for the plurality of medications. This embodiment can receive an incoming audio communication requesting information concerning a specific patient, such as a the side effects of a specific medication used by the patient. The audio communication from the patient contains a unique identifier which can be used as a key to query the database 214 for a set of one or more prescriptions identified for the patient in the host system database 214.

According to one aspect of the invention, the caller can choose a menu of medical information selections relating to the prescriptions identified for the patient, from which the caller can select one or more items. This, in turn, provides a selection signal to the system. This selection signal is then matched with a portion of the information in the database, which may, for example, relate to a specific medication. The system then provides an output which is representative of the selected portion of information and transmits a message to the caller.

Another telephony system of the present inventor is described in U.S. application Ser. No. 08/786,088, U.S. Pat. No. 5,737,396, issued Apr. 7, 1998, which is expressly incorporated by reference herein in its entirety. U.S. Pat. No. 5,737,396 describes a method of retrieving information relating to a patient's prescribed medication. A unique identifier is related to (or contains) the prescription number. A respectively different prescription number was assigned on a transactional basis to every prescription; a patient did not have a single identifier which could be used for all the patient's prescriptions.

A method or system according to the present invention does not rely on the entering of a prescription number, and may instead use any identifier unique to the patient, such as, for example, a password or social security number, which could be far easier to remember, and hence, more convenient for patients. More importantly, because the database is queried using an identifier of the patient as a database key, all the data attributes of the patient can be queried with a single identifier, including attributes which are not related to prescription medication.

It has been further determined that, by using a patient identifier to identify a list from which active items can be selected, the usability of voice recognition techniques is greatly enhanced. Optionally, once the patient is identified, vocalized queries related to medications are only compared to, or matched against, those medications for which this patient is associated. For example, rather than requiring the caller to say the name of the medication, which is then identified from an available list of 13,000 or more possible medication names, the present invention enables the system to look for a digitized medication name from a list of medications identified as "active" for this patient. For the vast majority of patients, fewer than ten medications are identified as, "active" at any one time.

The present invention permits patients to specify desired pharmacy functions, such as refilling, renewal, refill status, or educational information. The caller can select from a list of currently active prescription medications available on the host system database 216 for a particular patient. The list can be spoken out by the system first, so that the caller can select an item, or the caller can, alternatively, say the medication name and the interactive voice response system ("IVR") can use voice recognition techniques to select the correct medication from the small list of active medications for this particular patient. This approach allows a caller to use the system for four or more pharmacy functions without requiring him/her to remember all of his/her prescription numbers, as required by earlier systems. Optionally, the pharmacy function can be selected after the patient has identified the medication he/she wishes to investigate.

In addition to pharmacy functions, the caller (i.e., person) calling a system according to this invention can select one of a plurality of functions relating to other information on the patient's active profile on the host system without inputting further identifiers. For example, the caller might select to receive diagnosis and treatment information found in a patient's active profile. Given a database with pre-recorded information concerning diagnosis and treatment that can be mapped to the diagnosis and treatment signals on the host system database for the patient, the system can provide the caller the requested information. The caller specifies whether information relevant to the disease condition is to be provided, including the treatment plan and dietary plans and other recommendations for the patient's condition and health. The IVR system provides information about the diagnosis and treatment plans. A status report could also be automatically provided to the physician, so that he or she knows that the patient has requested this information.

A caller can build his/her own database over the phone. In addition, a caller can augment the pharmacy database with information that is not in that pharmacy database. (For example, the user can add over-the-counter medications). A calling having access to a unique medication identification (e.g., National Drug Code) can create medication lists or add to the pharmacy database intelligently. Preferably, this medication identifier appears on the label of the medication.

Other examples of relevant functions that can be mapped to a patient's active profile include information relevant to inpatients in a hospital. Upon providing a patient identifier commonly known to family and friends such as the patient's home phone number, the system can uniquely identify the patient from among all inpatients in the host database. By mapping the phone number to the patient's room, calls can be automatically transferred to the patient, to the nurse's station responsible for the patient, or to public information that hospital staff may want to provide callers about that inpatient, such as how well they spent the night and how they are eating. Similarly, this invention may be applied to hotel and motel settings, wherein guests can be automatically contacted by outside callers through a host database lookup of the guest's home phone number or office number, for example, which is provided by the guest during check-in.

A hotel chain could also use this feature to allow an outside caller to call a central telephone number, specify a desired party's home or office phone number, and direct a telephone call or voice mail message to the desired party staying with the hotel chain, without knowing at which of the chain's locations the party is staying.

By providing a patient identifier accessible to staff, such as an internal patient ID, staff members can exchange information relevant to that patient such as diagnosis information and other comments about that patient. Preferably, such information would only be made available to authorized staff or providers.

A preferred version of this invention can operate with the popular MUMPS database used by many pharmacy management systems. It is understood that this invention can operate using existing IVR hardware and software, database access technologies including a system server, voice database, voice synthesizer or audio recordings, and personal computers.

The inventor also contemplates providing additional functionality in this system, such as pharmacy-related operations, with or without the input of a prescription number. A flow chart diagram of an improved interactive system 200 is shown in FIG. 2. For example, the patient or care giver can call 210 and input a unique identifier 212 which is a personal identifier, such as a social security number, telephone number, and may include a pass validation, such as password. Next, the system validates the patient identifier 214 and searches a host system database for the patient's active profile 216. The active profile can describe the patient's diagnosis and treatment plan, including all of the patient's active prescriptions, identified with separate prescription numbers. The system can then provide a list of function options 218 that are available for that particular caller.

For example, the menu of options may include (1) refill or renew prescription, (2) check on refill status, (3) get educational information about patient's (a) medications, (b) diagnosis information, (c) treatment plans, (d) patient's status, etc. The caller next selects the desired function 220. Using the unique identifier as a key, the system searches the external host system database, or databases, to retrieve relevant information from the patient's active profile 216. If the caller selects a pharmacy function such as prescription refills, renewals, or refill status functions, he or she can select from active prescriptions from a host system for a particular patient, or use voice recognition to select data from the active medications for that patient. The list of medications can be spoken out first for the caller to select an item from, for example, for CYLERT, press 1, for TRYPTOPHAN, press 2, etc. The system then posts the refill, renewal and status request to the pharmacy host system 224 and the results, if any, are returned to the caller, or provides the caller with educational information about the medication identified.

If the patient desires to learn information on diagnoses or treatment plans, he or she may select from active diagnoses 234. The system then searches treatment plans and other patient care information databases 228 and retrieves it for the caller.

Additionally, other information in the patient's active profile can be selected from the function menu 220. For this other information, which could include patient histories, blood type, family histories and other medical information, the patient can select an individual item from the active profile 236 which triggers the system to search for this other information on the patient's active profile in the host system database, or similar database 230, and respond in kind.

The disclosed telephony systems can be used with intranet or Internet-access terminals to provide easier access. The provided software can interact with multiple systems, such as voice-over telephone, devices for the deaf, network computers and browser access over the Web in digital or analog voice formats.

Advantageously, the application logic 310 operates independently of the media used to interact with the patient (voice 355, TDD 356, modem 357, Telnet 358, LAT 359, browser 360 or e-mail 361). This enables a single set of application code to drive all these media without special media-dependent logic for each medium. This is realizable using a "data dictionary" that maps between text, auditory or other signals and a tool set that selects which signal to present for each respective medium.

Presently known systems such as those provided by SmartTalk, Inc. or Televox, Inc. run as stand-alone systems without host interaction. They typically require patients to enter a topic identifier referred to as a "PIN" as well as their patient ID. These systems require the health care organization to give the patient a PIN for each instance in which the practice may deliver a message to the patient. The organization must then track that PIN and use it to post a message for the patient. For example, each time the patient gets a lab test, a new PIN is provided to the patient. When posting information for the patient, these prior systems require the health care organization to call the system and manually enter the topic PIN.

By contrast, the present invention can perform authentication using a patient ID, such as a social security number, patient identification number, or telephone number, against the host database and a separate transactional PIN is not needed for each topic. If a patient identification number is used, only one of these numbers need to be used to access all messages relevant to the patient. No existing system is known to automatically retrieve the patient's phone number from the host database to call the patient and notify the patient that there are messages for the patient, nor to automatically generate letters or e-mail with the text of the specified audio message and the patient address retrieved from the host database using the data dictionary feature described below.

Furthermore, users do not have to call into the exemplary system to post messages for patients. Users can select from pre-defined messages on the host database which we retrieve. Users can also record a message on their existing PC devices which are transferred to the exemplary system or they can have the exemplary system call them to make the private recording. The major advantage of this technique is that users (e.g., health care provider personnel) can post messages for patients without having to first: (a) dial into the system, (b) enter their provider IDs, (c) enter the patient IDs, and (d) enter the topic identifier ("PIN") in order to specify a message for the patient. Instead, the staff may already be signed onto their system and looking at information relevant to the patient (thus, items b & c are known to the host). They select the option that drives the exemplary system with their mouse, or touch tone pad, for example, and specify the message for the patient. To specify a message, the user can select from a list of canned messages or record a custom message using a voice card. If there is no voice card, the user can click on the option where the exemplary system calls them to make the recording.

In all instances, reports may be made available to document the transactions that have been performed.

The invention provides the capability to provide complete visual feedback on a screen even if the practice user is using a phone to post practice messages to the system (e.g., when the user enters the PID on a touch-tone phone, the system may display on a screen accessible to the caller complete demographic information about the patient so as to eliminate possible issues about entering data for the wrong patient.).

The invention eliminates a source of constant interruptions for providers and staff,. freeing them to focus their attention where it is needed most—on patients in the office. Record test results any time, from any phone. Allow patients to access test results 24 hours a day, 7 days a week. The invention "does the talking" when patients call to learn laboratory test results. By handling frequent calls from patients anxious to receive lab test results, the invention reduces constant interruption. The invention answers the calls and speaks a personal test result message—automatically. Productivity goes up, and patients have more quality time with their providers.

Using the invention, patients can access their test results 24 hours a day, 7 days a week. They simply dial the phone number and enter their patient ID (PID). The invention guides them through every call with easy-to-follow instructions. Available test results are spoken immediately. There is no waiting for records to be located or for providers to come to the phone. Patients with questions can record a message for their provider or, during office hours, can select the option to transfer to a "live" operator.

Providers and authorized personnel can record patients' test result messages at their convenience, from any telephone. Standard messages for routine results can be recorded once, saved, and re-used. Any authorized provider can assign these messages to patients with identical lab test results or add a personal message, as needed.

All calls are logged. Call results can be viewed on the monitor or printed for verification of the date the message was given. All messages, including personal instructions from the provider, can be archived on tape, retrieved by batch and authorization number, and listened to for verification of exactly what patients were told.

More than one provider can select or record messages for a single patient. When the patient calls in, messages are played, oldest to newest. They can be listened to an unlimited number of times during a designated period, with the option to skip forward to the next message.

An exemplary block diagram of the system 300 is shown in FIG. 3. The system includes a telephony server 330, which isolates the medical/pharmaceutical application programs from the hardware. Server 330 includes separate interfaces for each of the different media that communicate with system 300. Telephony server 330 may include known storage media for storing pre-recorded messages, and voice synthesizing means for generating any arbitrary message used by the system. Telephony server 330 may also include voice recognition means.

Telephony interface 340 is provided for communications with telephone users 355 over public telephone networks 354. The telephony interface 340 allows system 300 to communicate with a telephone keyset 355 as an Input/Output (I/O) device.

Server 330 has serial ports 350 and 351 for interfacing to a TDD modem 352 and a standard computer modem 353, respectively. TDD modem 352 communicates with a TDD user 356 over the public telephone network 354. Standard computer modem 353 communicates with modem users or computer systems 357 over the public network 354. System/network printer/fax and e-mail services may be accessed as required using standard techniques.

Besides the public network users, server 330 can also communicate with computers in a proprietary enterprise network—which may be a local area network (LAN) or a wide area network (WAN)—or a global communications network 375, such as the Internet. A Telnet user 358 can communicate with server 330 (for example, using terminal emulation) via the enterprise network 375, using Telnet port 370. An LAT user 359 can communicate across enterprise network 375 via LAT port 371. A browser user 360 can communicate with server 330, via browser port 372. An electronic mail (e-mail) system 373 may be provided.

When the application 310 is going to perform an I/O operation, the application 310 needs only determine what to input or output. The Mumps talk environment determines what type of user 355–361 is communicating with the application. The Mumps talk environment 325 determines the format that is needed, i.e., whether it is textual, or sound-based. The Mumps Talk Data Dictionary 321 is used to retrieve what the application wants to say, either in sound format or in text format. In general, when data (messages) are input to the system to build the data dictionary 321, the data are input in both the text representation 323 and the sound representation 322, in a one-to-one correspondence. When using a textual interface, (browser 372, LAT 371, Telnet 370, standard modem 353 or TDD modem 352, the text version 323 is retrieved.

When dealing with a sound-based interface, (telephony interface 340) the sound representation 322 is used. Sound representation 322 could also be used for the TDD interface if, instead of transmitting via a serial device, the system is playing TDD recordings. Similarly, one could play sound recordings over the browser connection 372 as well. In any of these specific instances a Mumps talk data dictionary uses this sound representation 322. In every other instance, the text representation is used. The important feature is that, the application is always dealing with what it wants to say. The Mumps talk tool 325 figures out what the media is and what representation is needed; whether it is sound or text. In addition the Mumps talk environment 325 adds information such as HTML tags, or whatever is needed for the specific transaction. It retrieves the actual text and it will encouch it with media-specific formatting. The data dictionary 321 manages the various representations, either sound 322 or text 323. The Mumps talk tool 325 grabs the appropriate representation based for the medium that is being used and then massages it as needed.

The default interface used is the telephone interface 340. If the user does not have a TDD modem, telephony is used. The telephony side is always enabled, the other interfaces may or may not be enabled. In a variation of the exemplary embodiment, the patient's profile may include a parameter which determines which type of user device 355–361 is used for outgoing messages, when contacting the patient. The system can also mail a letter to the patient with the text that would have been spoken to the patients. If the patient does not call within a certain parameter of time, then the text of the message is sent to the printer interface 374.

Although the exemplary embodiment uses the Mumps talk tool, other tools may be used to provide similar functionality. The interface needs the ability to determine what type of device 355–361 is that it is communicating with, and then based on that device, it will select what medium (text or sound) is appropriate to send outgoing communication to that device. Further, if text is used, the interface determines whether to put any special control information around the text.

Advanced Appointment Reminder Functions

According to another aspect of the invention, improved results are obtained by several improvements in appointment reminder methods.

According to one aspect of the invention, the system 300 identifies patients with phone number or phone line problems in advance of the date on which the system will place a call to the patient. Patients' phone numbers are validated well before a patient's appointment date, and any patient having problems in his/her phone number is identified (including missing area code, a local exchange that doesn't match the area code, an exchange of a seven-digit number that doesn't match the default area code for a seven-digit number, or a phone number that has an incorrect number of digits). If the problem is not corrected by the time system 300 needs to send a message to the patient, the message is sent by mail. This helps ensure that nearly 100% of the patients are contacted.

Reports may be sorted by user and are printable on any printer to which the host system can print. This enables each clinic in a large organization to conveniently receive important reports at their local printer, concerning the patients contacted for their clinic. Further, clinic staff are alerted to "phone company intercept tones." First, the intercept tones identify: (a) numbers that are incorrect; (b) disconnected; or (c) changed. Second, the system alerts the specific staff person who is to interact with the patient, by printing a notification to the most convenient printer. Third, the system posts back to the host an alert, so that staff can verify the complete patient demographic information, particularly address. This function takes advantage of the fact that a change in phone number is often accompanied by a change in address. Thus, the user has an automatic tool to detect many address changes for active patients. This enables users in the clinic to update the patient profiles for active patients who have changed telephone numbers.

Because of the above-mentioned statistics (described with reference to FIG. 4), the system 300 is able to identify patients who have a "no-show" history, or fail to keep their scheduled appointments. System 300 can automatically schedule an extra telephone call reminder for these patients. This reduces the "no-show" rate and helps ensure that patients receive the proper care.

Another optional function is the ability to place an advance call or send an e-mail to non-local patients. This function provides out-of-zone patients extra time to make travel arrangements.

The invention provides an important service to patients through consistent, personalized appointment and rescheduling reminders. The invention consistently reminds patients of their appointments. Appointment slots can be more effectively filled with patients who confirm they will be there. Staff members are freed from reminding hundreds of patients by phone calls or mailings. The efficiency of the entire office increases.

Using the invention, patients actively confirm that they will keep appointments through a touch-tone or spoken yes/no response. Patients who indicate they can't keep their appointments are given a reminder to reschedule. If calls are placed during business hours, patients can be given the option to transfer the call to the scheduling desk. Transfer hours can vary from office to office. A printed system report can verify all call results.

Patient privacy can be protected. According to one embodiment of the invention, the system provides an identification that only the patient or a family member would recognize as belonging to the patient (e.g., part of a social security number, birth date, or mother's maiden name). The person receiving the call must confirm the name of the patient for authentication. If the patient is at home, the system waits until the patient comes to the phone before speaking the reminder.

System reports can be sorted by provider or office and directed to fax machines, printers, or files in multiple locations, saving time and money. A variety of reports tell providers which patients are confirmed or unable to keep their appointments. Importantly, this information is posted back to the host patient scheduling system, which is used by the site for workload planning and management, well in advance of the day the appointments take place.

Variations of the exemplary embodiments may add further functionality. Dialing result controls allow the user to determine the days and times to dial, and to base the intervals between contact attempts on the result of each call (i.e., busy, no answer, answer/no response). The invention can screen out answering machines or leave a message after a pre-determined number of attempts. Further, patients themselves can access the system via phone call or Internet to configure a personal profile of how the system is to contact them. This personal profile may include: phone numbers, days and time of day to contact the patient, e-mail address, beeper number, or other parameter of importance to the patient.

Unforeseen schedule changes often necessitate notifying large blocks of patients that their appointments must be rescheduled. The invention can deliver a message to a block of patients. This may include automatic transfer of the call to the scheduling desk when the patient is reached, or may include a request that patients call the office number during designated hours.

Further, although this reminder function is well suited for reminding patients of their appointments, it is also useful for reminding patients that a bill payment is due. Using the same functions, a practice can include reminder messages for billing. The effectiveness of the patient reminder can be tracked and reported, based on payments made, and posted back to the host system.

The present invention may be embodied in the form of computer-implemented processes and apparatus for practicing those processes. The present invention may also be embodied in the form of computer program code embodied in tangible media, such as floppy diskettes, read only memories (ROMs), CD-ROMs, hard drives, ZIP™ drives, JAZ™ drives, or any other computer-readable storage medium, wherein, when the computer program code is loaded into and executed by a computer, the computer becomes an apparatus for practicing the invention. The present invention may also be embodied in the form of computer program code, for example, whether stored in a storage medium, loaded into and/or executed by a computer, or transmitted over some transmission medium, such as over the electrical wiring or cabling, through fiber optics, or via electromagnetic radiation, wherein, when the computer program code is loaded into and executed by a computer, the computer becomes an apparatus for practicing the invention. When implemented on a general-purpose processor, the computer program code segments configure the processor to create specific logic circuits.

Although the invention is described in terms of exemplary embodiments, it is not limited thereto. Rather, the appended claims should be construed to include other variants and embodiments of the invention which may be made by those skilled in the art without departing from the true spirit and full range of equivalents of the appended claims.

What is claimed is:

1. An automated telephony method of providing information relating to a patient in response to an incoming audio communication from a caller, comprising the steps of:

(a) providing a database containing information representing attributes of each of a plurality of patients;

(b) receiving an incoming audio communication via a telecommunications network, said audio communication containing a unique identifier which is associated with a specific one of the patients in said database;

(c) identifying a list of selectable operations to the caller, the list of selectable operations being specific to said specific patient;

(d) selecting one of said selectable operations to provide a selection signal, the caller performing said selection;

(e) matching said selection signal with a portion of the medical information in said database relating to said specific patient;

(f) providing an output containing verbal drug information to the caller, the output representing said portion of information relating to said specific patient.

2. The telephony method of claim 1 wherein said unique identifier comprises a portion of a social security number of the patient.

3. The telephony method of claim 1 wherein said unique identifier comprises a unique number which is dispensed to the patient in conjunction with a specific medication.

4. The telephony method of claim 1, wherein said selectable operations include at least one of the group consisting of obtaining information about common usage of a medication, obtaining information about side effects of the medication, obtaining information about drug-to-drug interaction.

5. The telephony method of claim 1 wherein said database comprises a pharmacy database or electronic patient record.

6. An automated telephony system for responding to an incoming audio communication from a caller, comprising:
a database containing information representing each of a plurality of patients;
sound processing means for receiving an incoming audio communication via a telecommunications network; said audio communication containing a unique identifier which is associated with a specific one of the patients in said database;
computer processing means for identifying a list of selectable operations to the caller, the list of selectable operations being specific to said specific patient;
said sound processing means including means for receiving a selection signal representing one of said selectable operations;
said computer processing means matching said selection signal with a portion of the medical information in said database,
wherein said computer processing means include:
means for displaying a menu containing a plurality of active prescriptions for said patient,
means for receiving a selection of one of said prescriptions, and
means for delivering a refill or renewal order, or performing a status check on the refill or renewal order.

7. The automated telephony system of claim 6, further comprising sound generating means for providing an output to the caller which is representative of said portion of information relating to said specific patient.

8. The automated telephony system of claim 6, wherein said unique identifier comprises a social security number.

9. An automated telephony method of providing information relating to a medication in response to an incoming audio communication, comprising:

(a) providing a database containing information for a variety of medications and a host system database containing signatures for at least some of said variety of medications;

(b) receiving an incoming audio communication relating to a request for information concerning a specific medication; said audio communication containing a unique identifier which can be mapped to a signature for said specific medication in said host system database;

(c) matching said identifier with a portion of the information in said database relating to said specific medication;

(d) providing a signal which is representative of said portion of information relating to said specific medication; and (e) transmitting a message containing verbal drug information concerning said specific medication generated from said signal which is responsive to said incoming audio communication.

10. The telephony method of claim 9 wherein said unique identifier comprises a prescription number.

11. The telephony method of claim 9 wherein said identifier comprises a unique number which is printed in human-readable form on a label of said specific medication.

12. The telephony method of claim 9, wherein said selectable operations comprise obtaining information regarding common usage, side effects, precautions for specific medication, drug-to-drug interactions, and general background information.

13. The telephony method of claim 9 wherein said database comprises a pharmacy database or electronic patient record.

14. An automated interactive telephony system comprising:

(a) a telephone voice processing receiving means for receiving an incoming telephonic audio inquiry relating to a request for specific medication information, said audio inquiry containing a unique identifier which can be mapped to a signature for said specific medication in a host system database;

(b) a medication information database containing information for a variety of medications;

(c) computer processing means for receiving said audio inquiry from said telephone voice processing receiving means, for matching said signature to a portion of the information in said medication information database relating to said specific medication, and for transmitting a signal which is representative of said information portion; and (d) telephone voice processing transmitter means for receiving said signal from said computer processing means and for sending an audio message containing verbal drug information relating to said specific medication which is responsive to said incoming audio inquiry.

15. A method for accessing medical information in a database, comprising the steps of:

(a) storing a plurality of data pertaining to a patient in a database;

(b) receiving an audio communication identifying the patient and a medication;

(c) automatically matching the medication identified in the audio communication with one of a plurality of known medications for which data are stored in the database; and (d) determining whether the medication identified in the communication has an interaction with a further medication the patient is taking, the determination being performed based on the plurality of data pertaining to the patient in the database.

16. A method according to claim 15, wherein the data pertaining to the patient in the database include at least one of the group consisting of: (i) prescription medicines the patient is taking; (ii) non-prescription medicines the patient is taking; (iii) a medical condition of the patient; and (iv) health-related information concerning the patient's lifestyle.

17. A method according to claim 15, further comprising, between steps (b) and (c), the step of determining whether the audio communication is being received from an authorized user of the database.

18. A method according to claim 15, wherein the audio communication is received via a telecommunication network.

19. A method according to claim 18, wherein the audio communication comprises human speech.

20. A method according to claim 18, wherein the audio communication is one of the group consisting of a dual-tone multi-frequency signal and a telephone device for the deaf (TDD) transmission.

21. A method according to claim 15, further comprising, between steps (a) and (b), the steps of:

(i) reading a human-readable identifier from a medication label, the human-readable identifier uniquely identifying a type of medication with which the label is associated; and (ii) forming the audio communication to include the human-readable identifier.

22. A method according to claim 21, wherein the human-readable identifier includes a portion of a national drug code associated with the type of medication with which the label is associated.

* * * * *